United States Patent [19]

Takahashi et al.

[11] Patent Number: 5,436,231
[45] Date of Patent: Jul. 25, 1995

[54] ADENOPHOSTINS

[75] Inventors: Shuji Takahashi; Masaaki Takahashi; Kazuhiko Tanzawa, all of Tokyo; Kaneo Ogawa, Iwaki; Tsuyoshi Hosoya, Tsukuba, all of Japan

[73] Assignee: Sankyo Company, Limited, Tokyo, Japan

[21] Appl. No.: 170,666

[22] Filed: Dec. 17, 1993

Related U.S. Application Data

[63] Continuation of Ser. No. 926,496, Aug. 7, 1992, abandoned.

[30] Foreign Application Priority Data

Aug. 14, 1991 [JP] Japan .................................. 3-204089

[51] Int. Cl.$^6$ ...................... A61K 31/70; C07H 19/20; C12P 19/12
[52] U.S. Cl. ............................. 514/47; 435/89; 536/26.21
[58] Field of Search ................... 536/26.21; 514/47; 435/89

[56] References Cited

U.S. PATENT DOCUMENTS 5,049,550  9/1991  Zamecik ........................... 536/26.2

FOREIGN PATENT DOCUMENTS 0344795  6/1982  European Pat. Off.
0249873  12/1987  European Pat. Off.
0359256  3/1990  European Pat. Off.
1506664  4/1978  Germany.

OTHER PUBLICATIONS

Roberts et al. Nature 265:279–281, 1977.
Farkas, et al. Collect, Czech. Chem. Comun. 42:909–930, 1977.
Berridge et al. Nature 341:197–205, 1989.
Furuichi et al. Nature 342:32–38, 1989.
Ferris et al. Nature 342:87–89, 1989.
Berridge et al. Nature 312:315–321, 1984.
Miyawaki et al. Neuron 5:11–18, 1990.
Maeda et al. J. of Neurochem. 51:1724–1730, 1988.
Ito, Masao, "Long-Term Depression," in Annual Review of Neuroscience, vol. 12, pp. 85–102, 1989.
Warsh et al. J. Neurochem. 56:1417–1422, 1991.
Berridge, Michael J., "Inositol Triphosphate and Di--Acylglycerol: Two Interacting Second Messengers," Annual Review of Biochem. 56:154–193, 1987.
Desai et al. Nature 348:66–69, 1990.
Roberts et al. Nature 265:379–381, 1977.
Farkas et al. Collect. Czech. Chem. Commun. 42:909–929, 1977.
Lee et al. J. Biol. Chemistry 264: 1608–1615, 1989.
Galione et al. Science 253:1143–1146, 1991.
Hirata et al. J. Biol. Chem. 264:20303–20308, 1989.
Prestwich et al. J. Am. Chem. Soc. 113:1822–1825, 1991.
Dreef et al. Tetrahedron Letters 32(42):6021–6024, 1991.

*Primary Examiner*—Douglas W. Robinson
*Assistant Examiner*—Gary L. Kunz
*Attorney, Agent, or Firm*—Frishauf, Holtz, Goodman & Woodward

[57] ABSTRACT

Compounds of formula (I):

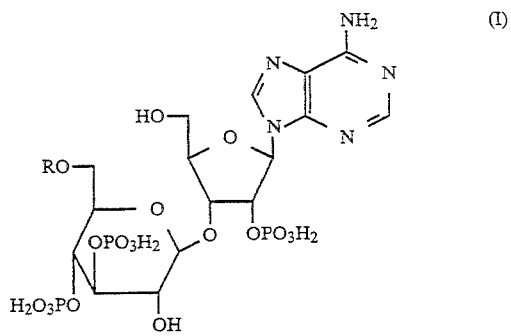

(wherein R represents a hydrogen atom or an acetyl group), which we have named "the adenophostins", and, have the ability to increase intracellular calcium ion concentrations by acting on the inositol 1,4,5-trisphosphate (InsP$_3$) receptors which exist in the endoplasmic reticulum. The adenophostins are useful as hypertensive agents. They can be prepared by cultivation of a microorganism of the genus *Penicillium*, e.g. *Penicillium brevicompactum* SANK 11991 (FERM BP-3499) or *Penicillium brevicompactum* SANK 12177 (FERM BP-3500).

11 Claims, No Drawings

ADENOPHOSTINS

This application is a Continuation of application Ser. No. 07/926,496, filed Aug. 7, 1992, now abandoned.

BACKGROUND TO THE INVENTION

The present invention relates to two new compounds which we have isolated from newly discovered strains of microorganism of the species *Penicillium*, as well as to salts and esters of these compounds. We have named the new compounds "the adenophostins". The invention also provides processes for the preparation of these compounds and methods and compositions using them for the treatment and prophylaxis of a variety of diseases and disorders resulting from an imbalance in the calcium ion concentration in the mammalian body.

The novel compounds of the present invention, adenophostins A and B, have the ability to increase intracellular calcium ion concentrations by acting on the inositol 1,4,5-trisphosphate ($InsP_3$) receptors which exist in the endoplasmic reticulum.

It is now well known that calcium ions play an important role in many cellular processes, including, for example, neural activity, muscle contraction, various secretion reactions and cellular growth and differentiation. Accordingly, the release of calcium ions into the cytosol is important to the operation of these processes, and compounds which have the ability to control this release clearly have great potential for use in therapy.

$InsP_3$ itself has an important effect on the release of calcium ions from internal stores to the cytosol [Nature 341, 197–205 (1989)]. InsP is produced in vivo from phospholipids which exist in cellular membranes by means of phospholipase C, which, in turn, may be activated by various hormones [Nature 312, 315–321 (1984)]. The $InsP_3$ thus produced binds to $InsP_3$ receptors located on the endoplasmic reticulum, where calcium ions are believed to be stored [Nature 342, 32–38 (1989)]. This binding results in activation of the calcium channels in the receptor, and calcium ions stored in the endoplasmic reticulum are released to the cytosol, thus elevating the cytosolic calcium ion concentration [Nature 342, 87–89 (1989); Neuron 5, 11–18 (1990)].

Like $InsP_3$, adenophostins A and B have the ability to bind to $InsP_3$ receptors, to open calcium channels in cells, especially the endoplasmic reticulum, and thus to elevate the cytosolic calcium ion concentration. The presence of a high concentration of $InsP_3$ receptors in cerebellar Purkinje cells suggests that InsP plays an important role in the development and differentiation of the nervous system [J. Neurochem. 51, 1724–1730 (1988)]. In addition, since long-term depression of the efficacy of synaptic transmission in Purkinje cells is believed to have some sort of memory function, $InsP_3$ is thought also to participate in cerebral learning and memory [Ann. Rev. Neurosci. 12, 85–102 (1988)]. A decrease in cerebral $InsP_3$ in patients with Huntington's disease (Huntington's chorea) has also been observed [J. Neurochem. 56, 1417–1422 (1991)], and, although a causal relationship has not been established, it is thought that administration of a compound having an activity equivalent to that of $InsP_3$ would alleviate the condition.

In addition, since it has been demonstrated that an elevation of the $InsP_3$-induced peripheral intracellular calcium ion concentration causes contraction of the smooth muscles, activation of the thymus-originated lymphocytes (T cells) and activation of pancreatic secretion [Ann. Rev. Biochem. 56, 159–193 (1987): Nature 348, 66–69 (1990)], compounds having an $InsP_3$-like ability to open calcium channels are expected to be useful as hypertensive agents because of their contractive action on vascular smooth muscles, as immunoactivating agents because they activate the immunocompetent cells and for the treatment of type I diabetes mellitus by accelerating insulin secretion.

The adenophostin compounds of the present invention are adenosine derivatives which additionally contain a structure similar to, but different from, that of inositol phosphate.

A number of adenosine derivatives is known as microbial second metabolites. For example, agrocin [Nature, 265, 379–381 (1977)] and thuringiensin [Collection of Czechoslovak Communications, 42, 909–929 (1977)] are adenosine derivatives and include a phosphate group in the molecule, like the adenophostins, but they differ structurally from adenophostins A and B. Moreover, these compounds are reported to have different activities to those of adenophostins A and B, and there have been no reports of which we are aware suggesting that they have the same effect on $InsP_3$ receptors as do adenophostins A and B, or that they influence release of calcium ions.

Cyclic ADP-ribose is an adenosine derivative which induces calcium ion release from intracellular calcium ion stores in a manner apparently similar to that of the adenophostins and $InsP_3$ [The Journal of Biological Chemistry, 264, 1608–1615 (1989)]. However, it has been reported that the action of cyclic ADP-ribose is due to activation of the calcium-induced calcium release channel, not by activation of the $InsP_3$ receptors [Science, 253, 1143–1146 (1991)]. This finding is also reinforced by the fact that the structure of cyclic ADP-ribose is different from that of the adenophostins of the present invention.

Additionally, some inositol derivatives have been synthesized and found to act on the $InsP_3$ receptors [The Journal of Biological Chemistry, 264, 20303–20308 (1989). The Journal of the American Chemical Society, 113, 1822–1825 (1991): Tetrahedron Letters, 32, 6021–6024 (1991)], but these are not adenosine derivatives.

In summary, we are not aware of the disclosure of any adenosine derivatives, which possess an activity similar to that of $InsP_3$.

BRIEF SUMMARY OF THE INVENTION

It is an object of the present invention to provide certain new compounds having $InsP_3$-like activity.

It is a further, and more specific, object of the present invention to provide such compounds which can be used for the treatment and prophylaxis of a variety of diseases and disorders resulting from an imbalance in the body's calcium supply.

Other objects and advantages will become apparent as the description proceeds.

The compounds of the present invention are those compounds which may be represented by the formula (I):

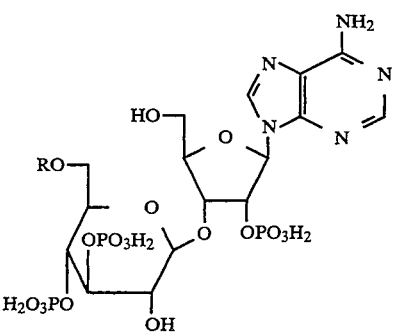

wherein R represents a hydrogen atom or an acetyl group, and salts and esters thereof.

These compounds have been named by us "the adenophostins", that compound in which R represents a hydrogen atom being adenophostin A, and that compound in which R represents an acetyl group being adenophostin B.

The invention also provides a process for preparing the adenophostins, which comprises cultivating an adenophostin-producing microorganism of the genus *Penicillium* and collecting at least one adenophostin from the culture. The resulting compound may then be subjected to conventional salification and/or esterification reactions to produce a salt or ester thereof.

The invention also provides a pharmaceutical composition comprising at least one adenophostin or a pharmaceutically acceptable salt or ester thereof in admixture with a pharmaceutically acceptable carrier or diluent.

DETAILED DESCRIPTION OF THE INVENTION

The adenophostin compounds of the present invention may be produced by microbiological processes, and thus it can be expected that they will be produced preferentially in a particular steric configuration. At present, it is believed that the compounds have the configuration shown in the following formula (Ia):

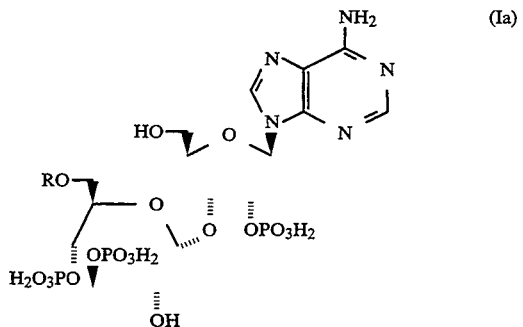

wherein R is as defined above. Although the present invention envisages the use of compounds of formula (I) having any configuration, the configuration shown above in formula (Ia) is preferred.

The adenophostins of the present invention may be prepared by culturing an adenophostin-producing microorganism of the genus *Penicillium*, and then collecting one or more of the adenophostins from the culture medium.

In particular, we especially prefer to employ as the microorganism one of two newly isolated strains of the genus *Penicillium*, which we have established belong to the species *Penicillium brevicompactum* and to which we have assigned the designations SANK 11991 (FERM BP-3499) and SANK 12177 (FERM BP-3500).

Strain SANK 11991 was deposited under the terms of the Budapest Treaty at the Fermentation Research Institute, Agency of Industrial Science and Technology, on 7th August 1991 with the accession no. FERM BP-3499, and Strain SANK 12177 was deposited under the terms of the Budapest Treaty at the Fermentation Research Institute, Agency of Industrial Science and Technology, on 7th Aug. 1991 with the accession no. FERM BP-3500.

In the following discussion of microbial properties, the colors are indicated by the code numbers proposed in the "Methuen Handbook of Colour" by A. Kornerup and J. H. Wanscher, published by Eyre Methuen, London, (1978).

Strain SANK 11991, which produces the adenophostins A and B, was isolated from a soil sample collected in Yubari City, Hokkaido, Japan. Details of the microbiological properties of this strain are shown below.

Colonies on Czapek yeast autolysate agar (CYA) medium were 16 mm in diameter (after growth at 25° C. for 7 days). A thick and dense hyphal mat was formed and the surface was downy. The colony was slightly protuberant at the center, and radially sulcate. The hyphae presented a white coloration, which was particularly remarkable at peripheral regions. Grayish green (26E3) conidia were formed at the center. An exudate was of-rmed, ranging in color from hyaline (i.e. clear and translucent) to golden yellow. No soluble pigments were produced. The reverse side presented yellowish brown (5D5), and was radially and concentrically sulcate.

Colonies on malt extract agar (MEA) medium were 16 mm in diameter (after growth at 25° C. for 7 days). A thick and dense hyphal mat was formed and the surface was velvety to downy, and plane. The hyphae presented a white coloration, which was particularly remarkable at peripheral regions. Grayish green to dull green (26E3) conidia were formed on almost the whole surface of the colonies, most particularly at the center. The reverse side presented grayish yellow (4B4).

Colonies on 25% w/v glycerol nitrate agar (G25N) medium were 7 mm in diameter (after growth at 25° C. for 7 days). A thin and dense hyphal mat was formed and the surface was velvety. The hyphae presented a white coloration. Grayish green (26D5) conidia were formed on almost the whole surface of the colonies, however not many conidia were produced. Conidia germinated at 5° C. to form microcolonies. At 37° C., no germination was observed on either Czapek yeast autolysate agar or malt extract agar medium. Conidiophores were formed aerially, mainly from hyphae on the medium. The walls were smooth. The penicilli were terverticillate but partly biverticillate. Metulae were cylindrical, and from 8 to 12 μm in length. Phialides were ampulliform, and from 6 to 12 μm in length. Conidia were spherical to subspherical and 2–6, more commonly 2–4, μm lonq. The walls of the conidia were smooth or very finely roughened. Conidia were borne on phialides in divergent and disordered chains.

Strain SANK 12177, which also produces the adenophostins A and B, was isolated from a soil sample collected in Fukue City, Nagasaki Prefecture, Japan. Details of the microbiological properties of this strain are shown below.

Colonies on Czapek yeast autolysate agar medium were 36 mm in diameter (after growth at 25° C. for 7 days). A thick and dense hyphal mat was formed and the surface was velvety. Downy hyphae developed towards the center. The colony was slightly protuberant at its center and radially sulcate. The hyphae presented a white coloration. Conidia were formed on the whole surface of the colony, and were dull green (25E3) in color. A greenish yellow (1AS) exudate was formed, and a soluble pigment of the same color was excreted into the medium. The reverse side presented grayish yellow (4C6), and was radially and concentrically sulcate.

Colonies on malt extract agar medium were 33 mm in diameter (after growth at 25° C. for 7 days). The surface was velvety and plane. The hyphae presented a white coloration, which was particularly remarkable at the peripheral regions of the colony. Conidia were dull green (25D3) in color, and were formed on almost the whole surface of the colonies. The reverse side presented dark yellow (4C8).

Colonies on 25% w/v glycerol nitrate agar medium were 26 mm in diameter (after growth at 5° C. for 7 days). A thin and dense hyphal mat was formed and the surface was velvety. The central part was protuberant. Dull green (25E3) conidia were formed on almost the whole surface. The conidia germinate at 5° C. to form microcolonies. At 37° C., no germination was observed on either Czapek yeast autolysate agar or malt extract agar medium. Conidiophores were formed aerially mainly from hyphae on the medium. The walls were smooth. The penicilli were terverticillate, but partly biverticillate. Metulae were cylindrical, and were from 8.5 to 16.5 µm long. Phialides were ampulliform, and were from 6.5 to 13.5 µm long. Conidia were spherical to subspherical, and between 2 and 6, more commonly between 2 and 5, µm long. The walls of the conidia were nearly smooth. Conidia were formed on phialides in chains.

Based on these properties, the mycological properties of these strains were found to accord with those of *Penicillium brevicompactum*, described by Pitt [J. I. Pitt: "The genus Penicillium and its teleomorphic states, *Eupenicillium* and *Talaromyces*", Academic Press, p. 371-375 (1979)].

Accordingly, strains SANK 11991 and SANK 12177 were identified respectively as *Penicillium brevicompactum* Dierckx SANK 11991 and *Penicillium brevicompactum* Dierckx SANK 12177.

It will be appreciated that strains SANK 11991 and SANK 12177, or any other strain capable of producing an adenophostin, may be sub-cultured or biotechnologically altered or modified to produce an organism with different characteristics. The only requirement is that the resulting organism be capable of producing the required compound. Alterations may occur naturally or artificially, by induction.

Such alterations and modifications may take any desired form, or may be consequent on such considerations as culture conditions, for example. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility. or combinations thereof, in order to maintain purity, or to allow purification of cultures, especially seed cultures, from time to time.

Other characteristics which may be introduced by genetic manipulation are any that are permissible in *Penicillium* spp. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring *Penicillium* plasmid and inserting a desired gene or genes from another source. Natural plasmids may also be modified in any other manner that may be considered desirable.

Any such modified strain may be employed in the process of the present invention, provided only that the strain is capable of producing an adenophostin, a matter which can readily be ascertained by simple and routine experimentation.

In order to obtain an adenophostin from a culture of a suitable microorganism, the microorganism should be fermented in a suitable medium. Such media are generally well known in the art, and will frequently be of a type commonly used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism.

Suitable carbon sources include, for example: glucose, fructose, maltose, sucrose, mannitol, glycerol, dextrin, oatmeal, rye, corn starch, potato, potato starch, corn powder, soybean meal, cottonseed oil, molasses, citric acid and tartaric acid, any of which may be employed alone or in combination with any one or more others. Typical amounts will be in a range from about 1 to 10% w/v of the amount of medium, although the amount may be varied as desired and in accordance with the desired result.

Suitable nitrogen sources include any substance containing a protein, for example, or other readily assimilable source of nitrogen. Representative examples of nitrogen sources are organic nitrogen sources from animals and plants, and may be extracts from such natural sources as soybean meal, wheat bran, peanut meal, cottonseed meal, cottonseed oil, casein hydrolysate, fermamine, fish meal, corn steep liquor, peptone, meat extract, yeast, yeast extract and malt extract: and such inorganic nitrogen sources as sodium nitrate, ammonium nitrate and ammonium sulfate. As with the carbon source, these may be employed alone or in any combination. Suitable amounts are typically within a range from about 0.1 to 6% w/v of the amount of medium.

Suitable nutrient inorganic salts are those which provide trace elements as well as the major constituent of the salt. Preferably, salts should provide such ions as sodium, ammonium, calcium, phosphate, sulfate, chloride and carbonate. Such trace metals as potassium, cobalt, manganese, iron, magnesium and strontium, or salts capable of providing such ions as bromide, fluoride, borate or silicate ions, may also be present.

If the microorganism is fermented as a liquid culture, it is preferred that an antifoaming agent, such as a silicone oil or vegetable oil, or other suitable surfactant, is employed.

It is preferred that the pH of the culture medium for the cultivation of Penicillium brevicompactum Dierckx strains SANK 11991 and SANK 12177, when used for the production of an adenophostin, should be maintained in the region of pH 5.0 to pH 7.0, although the only requirement is that the pH should not prevent growth of the microorganism, or adversely irreversibly affect the quality of the final product.

*Penicillium brevicompactum* Dierckx strains SANK 11991 and SANK 12177, in general, grow at temperatures ranging from 5° C. to 32° C., and grow well at from 22° C. to 30° C. Other temperatures not falling within these ranges may be applicable where a strain has been developed which can grow at lower or higher temperatures, or for other special purposes, as is well known in the art. For the production of an adenophostin, a preferable temperature is between 22° C. and 28° C.

The adenophostins are ideally obtained by aerobic culture, and any suitable aerobic culture techniques, such as, for example, solid culture, shaking culture or aeration-agitation culture may be employed.

If the culture is conducted on a small scale, then a shaking culture fermented for several days at from 22° C. to 26° C., more preferably about 26° C., is generally preferred.

To start a fermentative culture, a preferred technique employs an initial inoculum prepared in one or two steps, for example, in an Erlenmeyer flask, which is preferably provided with baffles (a water flow controlling wall). A carbon source and a nitrogen source may be used in combination for the culture medium. The seed flask is shaken in a thermostatic incubator at 26° C. for a period of from 2 to 7 days, or until sufficient growth is observed. The resulting seed culture may then be used to inoculate a second seed culture, or a production culture. If a second seeding is conducted, this may be performed in a similar manner, and partly used for inoculation to the production medium. The flask into which the seed culture is inoculated is shaken for a suitable period, for example from 2 to 7 days, or until maximal production is obtained, at a suitable temperature, for example 26° C. When incubation is complete, the contents of the flask may be collected by centrifugation or filtration.

If the culture is to be performed on a large scale, cultivation in a suitable aeration-agitation fermenter may be preferable. In this procedure, the nutrient medium can be prepared in a fermenter. The medium is first sterilized at 125° C., after which it is cooled and seeded with an inoculum previously grown on a sterilized medium. The culture is preferably performed at a temperature from 22° C. to 26° C., preferably 26° C., with stirring and aeration. This procedure is suitable for obtaining a large amount of the compound.

The amount of the adenophostins produced by the culture with the passage of time can be monitored by sampling and assessing the inhibitory activity of the sample, as explained below in Test Example 1. In general, the amount of adenophostin A or B produced reaches a maximum after a period of time of between 72 hours and 168 hours.

After a suitable period of culture, the desired adenophostin or adenophostins may be isolated and purified by any known means. For example, any adenophostin remaining in the culture broth may be obtained by filtering off the mycelia and any other solids, for example, using diatomire as a filtration aid, or by centrifugation and subsequent extraction from the supernatant by purification using techniques depending on the physicochemical properties of the desired adenophostin. For example, any adenophostin A or B existing in the filtrate or in the supernatant can be extracted using an adsorbent, for example active carbon or an adsorbing resin such as Amberlite XAD-2, XAD-4 or XAD-7 (trade names for products of Rohm & Haas Co.) or Diaion HP-10, HP-20, HP-20AG or HP-50 (trade names for products of Mitsubishi Kasei Corporation) may be employed. Impurities can be removed by adsorption by passing the liquid containing the adenophostin or adenophostins through a layer of the adsorbent and then the adenophostin may be recovered from the liquid passing through the layer of adsorbent. Alternatively, adenophostin A or B can be adsorbed on the layer of adsorbent, and then eluted with a suitable eluent, such as aqueous methanol, aqueous acetone or butanol/water.

Alternatively, because they are acidic, adenophostin A or B can be adsorbed on an anionic or cationic exchange material, and then recovered by elution. Examples of anion exchange materials which may be employed include diethylaminoethyl cellulose, diethylaminoethylSephadex, QAE-Sephadex ("Sephadex" is a trade name for a product of Pharmacia Fine Chemicals Inc.), Duolite A-2 (a trade name for a product of Diamond Shamrock Chemical Corp.), Amberlite IRA-68 (a trade name for a product of Rohm & Haas Co.), Dowex 1X4, 21K or SBR-P (trade names for products of Dow Chemical Co.). Examples of cation exchange materials which may be employed include Amberlite IRC-50 (a trade name for a product of Rohm & Haas Co.) or Dowex 50W (a trade name for a product of Dow Chemical Co.). As a further alternative, because of their acidic properties mentioned above, adenophostin A or B can be extracted in the form of a quarternary ammonium salt from an aqueous solution by dissolving a quarternary ammonium salt such as dimethyl benzylcetyl ammonium chloride in a water-immiscible solvent such as methylene chloride, mixing the solution with a mixture containing the adenophostin A and/or B, and then extracting the adenophostin A and/or B with water. Adenophostin A and/or B present in the mycelia can be obtained by extraction with 50-90% by volume aqueous acetone or aqueous methanol, followed by removal of the organic solvent, after which the extract may be subjected to similar extraction and purification procedures as those described above for the flitrate.

The resulting adenophostin A or B may be further purified by well known techniques, for example: by adsorption column chromatography using a carrier, such as silica gel or magnesium-silica gel, for example that sold under the trade name "Florisil"; by partition column chromatography using an adsorbent such as Sephadex LH-20 (a trade name for a product of Pharmacia Fine Chemicals Inc.), Toyopearl HW-40 (a trade name for a product of Tosoh Co.) or Diaion CHP-20 (a trade name for a product of Mitsubishi Kasei Co.); or by high performance liquid chromatography using a normal phase or reverse phase column. As is well known in the art, these isolation and purification procedures may be carried out alone or in any suitable combination, and, if desired, repeatedly, to isolate and purify the desired final product.

Adenophostins A and B are novel compounds which have not previously been reported in the literature, and which have the ability to elevate the intracellular calcium ion concentration by binding to InsP receptors located on the endoplasmic reticulum. These compounds are, therefore, useful as hypertensive prophylaxis of cerebral diseases, such as senile dementia, Alzheimer's disease and Huntington's disease, as a result of their action on the brain. The compounds of the present invention are also useful as hypertensive agents.

The adenophostins of the present invention contain both an acidic group (the phosphoric acid groups) and a basic group (the amino group) and can thus form salts with either of these groups. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Because of the presence of the phosphoric acid groups, the compounds of the present invention can form salts with bases. Examples of such salts include: salts an alkali metal, such as sodium, potassium or lithium: salts with an alkaline earth metal, such as barium or calcium; salts with another metal, such as magnesium or aluminum; organic base salts, such as a salt with ammonia, methylamine, dimethylamine or dicyclohexylamine; and salts with a basic amino acid, such as lysine or arginine. The compounds of the present invention can also form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid, salts with arylsulfonic acids, such as benzenesulfonic acid or p-toluenesulfonic acid, salts with organic carboxylic acids, such as acetic acid, fumaric acid, tartaric acid, oxalic acid, maleic acid, malic acid, succinic acid or citric acid, and salts with amino acids, such as glutamic acid or aspartic acid.

The compounds of the present invention also form esters, because of the phosphoric acid groups. There is also no particular restriction on the nature of these esters, provided that, where they are intended for therapeutic use, they are pharmaceutically acceptable. Where they are intended for non-therapeutic uses, even this restriction does not apply.

Examples of groups with which the adenophostins of the present invention may form esters include:

$C_1$–$C_{20}$ alkyl groups, more preferably $C_1$–$C_6$ alkyl groups, such as the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylburyl, hexyl, isohexyl, heptyl, octyl, nonyl, decyl, dodecyl, tridecyl, pentadecyl, octadecyl, nonadecyl and icosyl groups, but most preferably the methyl, ethyl and t-butyl groups;

$C_3$–$C_7$ cycloalkyl groups, for example the cyclopropyl, cyclobutyl, cyclopentyl, cyclohexyl and cycloheptyl groups:

aralkyl groups, in which the alkyl part is a $C_1$–$C_3$ alkyl group and the aryl part is a $C_6$–$C_{14}$ carbocyclic aromatic group which may be substituted or unsubstituted and, if substituted, has at least one substituent selected from the group consisting of the substituents defined and exemplified below, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, m2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 2-nitrobenzyl, 4-methoxybenzyl and piperonyl groups:

alkeny groups such as the allyl, 2-chloroallyl and 2-methylallyl groups;

halogenated $C_1$–$C_6$, preferably $C_1$–$C_4$, alkyl groups in which the alkyl part is as defined and exemplified above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group: phenyl groups, which may be unsubstituted or substituted, preferably with at least one $C_1$–$C_4$ alkyl or acylamino group, for example the phenyl, tolyl and benzamidophenyl groups;

phenacyl groups, which may be unsubstituted or have at least one substituent selected from the group consisting of the substituents defined and exemplified below, for example the phenacyl group itself or the p-bromophenacyl group;

alkoxymethyl groups, in which the alkoxy part is $C_1$–$C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups;

5-alkyl or 5-phenyl [which may be substituted by at least one substituent selected from the group consisting of the substituents defined and exemplified below] (2-oxo-1,3-dioxolen-4-yl)alkyl groups in which each alkyl group (which may be the same or different) is $C_1$–$C_6$, preferably $C_1$–$C_4$, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

The substituents referred to above include the $C_1$–$C_4$ alkyl groups, $C_1$–$C_4$ alkoxy groups, $C_1$–$C_4$ haloalkyl groups, $C_1$–$C_3$ alkylenedioxy groups, halogen atoms, cyano groups and nitro groups.

The salts and esters may be formed by conventional salification and esterification reactions, which are well known in the art. In the case of the acid addition salts, because intramolecular salts may be formed between a phosphoric acid group and the amino group, it is preferred first to esterify the phosphoric acid groups before forming the acid addition salt. In the case of esterification, it is preferred first to acylate, e.g. acetylate, the hydroxy groups in the molecule.

When the compounds of the present invention are intended for therapeutic use, they may be administered alone or in a suitable pharmaceutical formulation containing, in addition to the active compound, one or more conventional diluents, carriers, excipients or adjuvants. The nature of the formulation will, of course, depend on the intended route of administration. However, for the oral route, the compound is preferably formulated as powders, granules, tablets, capsules or syrups. For parenteral administration, it is preferably formulated as an injection (which may be intravenous, intramuscular or subcutaneous) or as drops or suppositories. These preparations can be prepared by known means by adding such additives as vehicles, binders, disintegrators, lubricants, stabilizers, corrigents, solubilizing agents, suspending agents or coating agents. Although the dosage may vary depending upon the symptoms and age of the patient, the nature and severity of the disease or disorder and the route and manner of administration, in the case of oral administration to an adult human patient, the compounds of the present invention may normally be administered at a daily dose of from 10 mg to 1000 mg. The compounds may be administered in a single dose, or in divided doses, for example two or three times a day.

EXAMPLE 1

A) Culture

One loopful of spores of *Penicillium brevicompactum* Dierckx, strain SANK 11991 was inoculated into each of forty 500 ml Erlenmeyer flasks, each fitted with a baffle and each containing 100 ml of a sterilized medium having the composition shown below, and the microorganism was cultured for 7 days at 26° C. and whilst rotating at 200 rpm (7 cm radius of rotation), using a rotary shaker.

Composition of the medium:

| | |
|---|---|
| Glycerin | 50 g |
| Fresh potato | 50 g |
| Yeast extract | 5 g |
| Malt extract | 5 g |
| Deionized water to | 1000 ml | pH not adjusted

B) Isolation

The contents of all forty Erlenmeyer flasks, referred to above, were combined, to give 3 liters of a culture broth. 250 g of Celite 545 filter aid (a trade name for a product of Johns Manville Project Corporation, USA) were added to the combined culture broth, and the mixture was filtered to obtain a cake of the mycelia. The cake thus obtained was extracted by adding 1 liter of 80% by volume aqueous acetone, stirring for 0.5 hour and then removing the solvent by filtration. This procedure was repeated twice, to give 2 liters of a solution, from which the acetone was removed by evaporation under reduced pressure, using a rotary evaporator. Water was added to the residue to make a total volume of 500 ml, and then the pH of the solution was adjusted to a value of 3.0 by the addition of dilute aqueous hydrochloric acid. The solution was then passed through a column containing 300 ml of active carbon, which was washed with 1 liter of water and then with 50% v/v aqueous acetone, after which it was eluted with 50% v/v aqueous acetone containing 0.2 N ammonia. The aqueous ammoniacal acetone solution thus obtained was concentrated by evaporation under reduced pressure, using a rotary evaporator. The residue was then lyophilized, to afford 500 mg of a crude powder.

Three liters of the filtrate which had been separated from the mycelia by filtration, as described above, was passed through a column containing 300 ml of Diaion HP-20 (trade name). The liquid which passed through the column was then adjusted to a pH value of 3.0 by the addition of aqueous hydrochloric acid, after which it was passed through a column containing 300 ml of active carbon, was washed with water and then with 50% v/v aqueous acetone, and was eluted with 0.1 N aqueous ammonia. The eluate was concentrated by evaporation under reduced pressure, using a rotary evaporator, and was lyophilized, to afford 1.18 g of a crude powder. This crude powder was mixed with the crude powder obtained from the mycelia mentioned above for further purification, as described below.

1.6 g of the mixture of crude powders was dissolved in 500 ml of a 0.05M phosphate buffer (pH 6.8), and the resulting solution was applied to a column containing 100 ml of Sephadex DEAE A-25 (trade name) resin, which had previously been equilibrated with a 0.05M phosphate buffer (pH 6.8), and the column was then eluted with sodium chloride solutions containing a 0.05M phosphate buffer by gradually increasing the sodium chloride concentration. First, 500 ml of a 0.1M solution were used; this was followed by 500 ml of a 0.2M solution, 500 ml of a 0.3M solution, and 500 ml of a 0.5M solution. A solution containing the active fraction was collected from the eluate with the 0.3M sodium chloride solution. This solution was adjusted to a pH value of 3.0 by the addition of aqueous hydrochloric acid, after which it was charged onto a column containing 30 ml of active carbon, washed with water and eluted with 0.1 N aqueous ammonia. The eluate was concentrated by evaporation under reduced pressure, and was then lyophilized, to afford 39.4 mg of a powder containing adenophostins A and B.

In order to separate adenophostins A and B, high performance liquid chromatography was used. 39 mg of the crude powder containing adenophostins A and B were dissolved in 0.4 ml of water, and 0.1 ml of the resulting solution was injected into a Senshu pack, 4251-AQ column (Column size, 10 mm diameter by 250 mm long, Product of Senshu Scientific Co.). It was developed at a flow rate of 5 ml/minute, using a 0.05M phosphate buffer as the developing solvent. The active peaks were monitored by ultraviolet absorption at 260 nm. Adenophostin A was eluted in the period from 6 to 9 minutes. After 9 minutes, the developing solvent was changed to a 0.05M phosphate buffer containing 4% by volume acetonitrile, and the solution was developed at a flow rate of 5 ml/minute. Adenophostin B was eluted in the period from 12 to 15 minutes. This procedure was repeated 4 times, and the adenophostin A fractions and adenophostin B fractions were collected separately. Each of the fractions was desalted, using active carbon. Aqueous hydrochloric acid was added to each of the adenophostin A and adenophostin B fractions, to adjust its pH to 3.0. Each fraction was then separately applied to a column containing 3 ml of active carbon, washed with water and then eluted with 0.1 N aqueous ammonia. Each of the eluates was concentrated by evaporation under reduced pressure, using a rotary evaporator, and lyophilized, to afford 10 mg of adenophostin A and 10 mg of adenophostin B each as white powders.

Adenophostin A was found to have the physicochemical properties shown below:

1) Nature and appearance: An acidic, water-soluble white powder.

2) Optical rotation:
$[\alpha]_D^{25} = +28.6°$ (C=0.71, water).
3) Molecular formula: $C_{16}H_{26}N_5O_{18}P_3$.
4) Molecular weight: 669 (Determined by FAB-MS method) (FAB-MS is Fast Atom Bombardment Mass Spectrometry).
5) Elemental analysis: Calculated as $C_{16}H_{26}N_5O_{18}P_3$ . diammonium salt . $3H_2O$ Calculated: C, 25.37%; H, 5.05%; N, 12.94%; P, 12.26%. Found: C, 25.52%; H, 5.03%; N, 12.85%; P, 11.32%.
6) Ultraviolet Absorption Spectrum, λmax nm (ε), determined in neutral, acidic or alkaline aqueous solution is as follows: In neutral aqueous solution: 258 (14,000). In acidic aqueous solution: 256 (13,300). In alkaline aqueous solution: 260 (14,000).
7) Infrared Absorption Spectrum, $\nu max$ $cm^{-1}$, determined by the potassium bromide pellet method, is as follows: 175, 1694, 1612, 1401, 1157, 1044, 940, 828.
8) $^1$H-Nuclear Magnetic Resonance Spectrum (δ ppm, 360 MHz) determined in deuterium oxide, and using the signal of water at 4.70 ppm as a reference, is as follows: 3.75–3.92 (5H, multipier); 4.05 (1H, doubled doublet of doublets); 4.47 (1H, doublet); 4.50 (1H, doubled doublet of doublets); 4.64 (1H, quartet); 5.29 (1H, multiplet); 5.33 (1H, doublet); 6.30 (1H, doublet); 8.27 (1H, singlet); 8.38 (1H, singlet).
9) C-Nuclear Magnetic Resonance Spectrum: (6 ppm, 90 MHz) determined in deuterium oxide, using the signal of dioxane (δ=67.00 ppm) as the internal standard, is as follows: 54.0 (singlet); 50.0 (doublet); 48.9 (singlet); 42.5 (doublet); 19.6 (singlet); 8.5 (doublet); 7.9 (doublet); 5.1 (doublet); 77.7 (doublet); 75.8 (doublet); 74.4 (doublet); 73.1 (doublet); 72.3 (doublet); 71.3 (doublet); 61.8 (triplet); 60.7 (triplet).
10) Solubility: Soluble in water and dimethyl sulfoxide; slightly soluble in lower alcohols, such as methanol or ethanol; insoluble in acetone, ethyl acetate or chloroform.
11) High performance liquid chromatography: Separating column; YMC Pack AQ-312 (Column size, 6 mm diameter by 150 mm long, Product of Yamamura Chem. Lab. Co.Ltd.) Mobile phase: 2% by volume acetonitrile in a 0.1M phosphate buffer (pH 6.8) Flow rate: 1.5 ml/minute Detecting wave length: Detection by means of a photodiode array throughout the wavelength from 220 nm to 400 nm Retention time (Rt value): 3.24 minutes.
12) Thin layer chromatography: Rf value 0.11 Adsorbent: silica gel plate No. 5715 (Product of Merck & Co., Inc.) Developing solvent: a 15:10:3:12 v/v mixture of butanol, pyridine, acetic acid and water Detection: Ultraviolet lamp (254 nm) or color development by use of $H_2SO_4$.

Adenophostin B was found to have the physicolchemical properties shown below:
1) Nature and appearance: An acidic, water-soluble white powder.
2) Optical rotation: $[\alpha]hd\ D^{25} = +33.8°$ (C=0.91, water).
3) Molecular formula: $C_{18}H_{28}N_5O_{19}P_3$.
4) Molecular weight: 711 (Determined by FAB-MS method).
5) Elemental analysis: Calculated as $C_{18}H_{28}N_5O_{19}P_3$ . diammonium salt . $4H_2O$ Calculated: C, 26.45%; H, 5.18%; N, 11.99%: P, 11.36%. Found : C, 26.43%; H, 4.77%; N, 11.66%; P, 10.80%.
6) Ultraviolet Absorption spectrum, $\lambda_{max}$ nm (ε) determined in neutral, acidic or alkaline aqueous solution, is as follows: In neutral aqueous solution: 258 (13,300). In acidic aqueous solution: 256 (13,000). In alkaline aqueous solution: 260 (13,300).
7) Infrared Absorption spectrum, $\nu_{max}$ $cm^{-1}$ determined by the potassium bromide pellet method, is as follows: 3128, 1730, 1693, 1613, 1508, 1401, 1235, 1159, 1090, 1040, 943.
8) $^1$H-Nuclear Magnetic Resonance Spectrum: (δ ppm, 360 MHz), determined in deuterium oxide, using the signal of water at 4.70 ppm as a reference, is as follows: 2.11 (3H, singlet); 3.80 (1H, multipier); 3.87 (2H, doublet of doublets); 4.05 multipier); 4.15 (1H, doubled doublet of doublets); 4.26 (1H, doublet of doublets); 4.45–4.56 (3H, multiplet); 4.62 (1H, quartet); 5.29 (2H, multipier); 6.33 (1H, doublet); 8.42 (1H, singlet); 8.51 (1H, singlet).
9) $^{13}$C-Nuclear Magnetic Resonance Spectrum: (δ ppm, 90 MHz), determined in deuterium oxide, using the signal of dioxane (δ=67.00 ppm) as the internal standard, is as follows: 174.4 (singlet); 150.8 (singlet); 148.8 (singlet); 145.4 (doublet); 143.8 (doublet); 119.5 (singlet); 98.5 (doublet); 87.7 (doublet); 84.9 (doublet); 77.6 (doublet); 75.9 (doublet); 74.5 (doublet); 73.4 (doublet); 71.0 (doublet); 69.8 (doublet); 63.8 (triplet); 61.5 (triplet); 20.6 (quartet).
10) Solubility: Soluble in water and dimethyl sulfoxide; slightly soluble in lower alcohols, such as methanol or ethanol; insoluble in acetone, ethyl acetate or chloroform.
11) High performance liquid chromatography: Separating column: YMC Pack AQ-312 (Column size, 6 mm diameter by 150 mm long, Product of Yamamura Chem. Lab. Co.Ltd.)
12) Mobile phase: 2% acetonitrile by volume in a 0.1M phosphate buffer (pH 6.8) Flow rate: 1.5 ml/minute Detecting wave length: Detection by means of a photodiode array throughout the wavelength from 220 nm to 400 nm Retention time (Rt value): 9.21 minutes.
12) Thin layer chromatography: Rf value 0.14 Adsorbent: silica gel plate No. 5715 (Product of Merck & Co., Inc.) Developing solvent: a 15: 10: 3: 12 v/v mixture of butanol, pyridine, acetic acid and water Detection: Ultraviolet lamp (254 nm) or color development by use of $H_2SO_4$.

EXAMPLE 2

A) Culture

One loopful of spores of *Penicillium brevicompactum* Dierckx, strain SANK 11991 was inoculated in a 2 liter Erlenmeyer flask containing 600 ml of a medium containing the same components as that described in Example 1, and the microorganism was cultured for 6 days at 26° C. and whilst rotating at 220 rpm, using a rotary shaker.

Meanwhile, 30 liters of a medium containing the same components as were used for the seed culture were put into a 60 liter stainless steel jar fermentor and heated for sterilization for 30 minutes at 120° C. 600 ml of the same seed culture as mentioned above were transferred into the fermentor. A second seed cultivation was carried out for 2 days at 26° C. at an aeration rate of 30 liters/minute, and whilst stirring at about 165 rpm (which was automatically controlled to keep the dissolved oxygen concentration at 5 ppm).

300 liters of a medium containing the same components as were used for the seed culture were placed in each of two 600 liter stainless steel tanks, which were then heated for sterilization for 30 minutes at 120° C. After this, 6 liters of the second seed culture were transferred into each tank, and the microorganism was cultured for 5 days at 26° C., at an aeration rate of 300 liters/minute, an internal pressure of 1.0 kg/cm$^2$ and a rotation rate of 82.5 rpm.

B) Isolation

A total of 680 liters of culture broth were obtained by the procedure described above. The whole of this was mixed with 20 kg of Celite 545 filter aid (a trade name for a product of Johns Manville Project Corporation, USA), and the mixture was filtered to separate the filtrate and mycelia. The mycelia thus obtained (66 kg) was extracted by the addition of 400 liters of 50% by volume aqueous acetone for 1 hour whilst stirring at room temperature, and then separating the resulting acetone solution. The extract was filtered again to separate the filtrate and the mycelia. 300 liters of 50% by volume aqueous acetone were added to the mycelia, and the mixture was stirred for 1 hour to extract further substances. The resulting extract was filtered and combined with that previously obtained. The acetone was removed from the combined extracts by evaporation under reduced pressure, to give 400 liters of an aqueous solution. This aqueous solution was passed through 60 liters of Diaion HP-20 (trade name), and then the pH of the solution was adjusted to a value of 3.0 by the addition of aqueous hydrochloric acid. The mixture was then charged onto a column containing 60 liters of active carbon, washed with 300 liters of water and then with 300 liters of 50% by volume aqueous acetone, and eluted with 450 liters of 50% by volume aqueous acetone containing 0.1 N aqueous ammonia. The eluate was concentrated by evaporation under reduced pressure, to give 10 liters of a condensed solution containing the active compounds.

The condensed solution was applied to a column containing 6 liters of Sephadex DEAE A-25 (trade name), which had previously been equilibrated with a 0.05M phosphate buffer (pH 6.8). The column was eluted with sodium chloride solutions which were made on the basis of 0.05M phosphate buffer solutions (pH 6.8) to which sodium chloride was added in increasing amounts. Thus, the column was first eluted with 30 liters of a 0.1M solution, next with 30 liters of a 0.2M solution, next with 30 liters of a 0.3M solution, next with 30 liters of a 0.4M solution, and finally with 30 liters of a 0.5M solution. The 0.3M sodium chloride solution was found to contain the active compounds, and a total of 17 liters of a solution containing the active fractions was collected.

Meanwhile, 660 liters of the filtrate separated from the mycelia by filtration were passed through a column containing 60 liters of Diaion HP-20 (trade name). Sufficient aqueous hydrochloric acid was then added to the resulting solution to adjust its pH to a value of 3.0, and then the solution was charged on a column containing 60 liters of active carbon. The column was washed with 300 liters of water and then with 300 liters of 50% aqueous acetone, after which it was eluted with 370 liters of 50% by volume aqueous acetone containing 0.1 N aqueous ammonia.

The aqueous ammoniacal acetone solution thus obtained was concentrated by evaporation under reduced pressure, to afford 10 liters of a condensed solution containing the active compounds. The condensed solution was applied to a column containing 6 liters of Sephadex DEAE A-25, which had previously been equilibrated with a 0.05M phosphate buffer (pH 6.8). The column was then eluted with sodium chloride solutions which were made on the basis of a 0.05M phosphate buffer (pH 6.8) to which sodium chloride was added in increasing amounts. Thus, the column was first eluted with 30 liters of a 0.1M solution, next with 30 liters of a 0.2M solution, next with 30 liters of a 0.3M solution, and finally with 30 liters of a 0.5M solution. The 0.3M sodium chloride solution was found to contain the active compounds, and a total of 10 liters of a solution containing the active fraction was collected. This solution was combined with the 17 liters of solution containing the active fractions previously obtained from the mycelia.

The combined active solutions were acidified by the addition of aqueous hydrochloric acid to a pH value of 3.0, and were then charged onto a column containing 500 ml of active carbon. The column was then washed with 5 liters of water, and eluted with 2.8 liters of 50% by volume aqueous acetone containing 0.1 N aqueous ammonia. The eluate thus obtained was concentrated by evaporation under reduced pressure and then lyophilized, to afford 9.01 g of a crude powder. The whole of this crude powder was dissolved in 2 liters of a 0.05M phosphate buffer (pH 6.8), and the resulting solution was applied to a column containing 500 ml of Sephadex DEAE A-25 (trade name), which had previously been equilibrated with a 0.05M phosphate buffer (pH 6.8). The column was eluted with sodium chloride solutions which were made on the basis of a 0.05M phosphate buffer (pH 6.8) to which sodium chloride was added in increasing amounts. Thus, the column was first eluted with 4 liters of a 0.1M solution, next with 4 liters of a 0.2M solution, next with 4 liters of a 0.3M solution, and finally with 4 liters of a 0.5M solution. The fractions eluted were monitored by their inhibitory activity and by high performance liquid chromatography. Those fractions eluted with sodium chloride solutions from 0.3M to 0.5M were found to contain the active fractions and gave a total of 1.5 liters of active fractions. The active fractions were acidified by the addition of aqueous hydrochloric acid to adjust their pH to a value of 3.0, and the resulting solution was then desaired, by charging the solution onto a column containing 100 ml of active carbon, washing the column with water and eluting it with 0.1 N aqueous ammonia. The eluate obtained was concentrated by evaporation under reduced pressure, and lyophilized, to afford 1.69 g of a crude powder containing adenophostins A and B.

In order to obtain pure adenophostins A and B from this crude powder, high performance liquid chromatography was employed. Specifically, 200 mg of the crude powder were dissolved in 2 ml of water, and 100 μl of this solution was injected into a Carbonex column (diameter 20 by 150 mm long, a trade name for a product of Tonen Co.) and then eluted at a flow rate of 8 ml/minute, using a 13% by volume mixture of acetonitrile and a 0.02M phosphate buffer (pH 6.8) as the developing solvent. The active peaks were monitored by ultraviolet absorption at 260 nm. Adenophostin A was eluted during the period from 6 to 8.5 minutes. Adenophostin B was eluted during the period from 9 to 15 minutes. Acetonitrile was removed from each of these active fractions by evaporation under reduced pressure, and each of the resulting condensed solutions was acidified by the addition of aqueous hydrochloric acid to adjust its pH to a value of 3,0; it was then desalted by adsorption on a column containing 10 ml of active carbon washing with water, and elution with 0.1 N aqueous ammonia. The eluted fraction was concentrated by evaporation under reduced pressure, using a rotary evaporator, and applied to a column (diameter 3 by 60 cm long) containing Sephadex LH-20; it was then eluted with water. The fractions eluted were monitored by high performance liquid chromatography, and single peaks corresponding to adenophostins A and B were obtained individually, These were lyophilized, and 30 mg of pure adenophostin A and 100 mg of pure adenophostin B were obtained separately, both as white powders. The properties of both compounds were the same as the properties of the compounds obtained as described in Example 1.

EXAMPLE 3

A) Culture

One loopful of spores of *Penicillium brevicompactum* Dierckx, strain SANK 12177 was inoculated into each of six 500 ml Erlenmeyer flasks, each fitted with a baffle and each containing 100 ml of a sterilized medium, whose composition is shown below. The microorganism was then cultured for 7 days at 26° C. and whilst rotating at 200 rpm (7 cm radius of rotation), using a rotary shaker.

Composition of the medium:

| | |
|---|---|
| Sucrose | 20 g |
| Fresh potato | 100 g |
| Polypeptone | 10 g |
| Potassium hydrogenphosphate | 5 g |
| Deionized water to | 1000 ml | pH not adjusted

B) Isolation

The culture broth thus obtained was centrifuged for 10 minutes at 5000 rpm, to give 500 ml of a supernatant. This was acidified by the addition of aqueous hydrochloric acid to adjust its pH to a value of 3.0 and then applied onto a column containing 50 ml of active carbon. The column was washed with 200 ml of water and then with 200 ml of 50% by volume aqueous acetone, after which it was eluted with 200 ml of 0.2 N aqueous ammonia. The solution thus obtained was concentrated by evaporation under reduced pressure. The resulting residue was then lyophilized, to afford a crude powder. The whole of this crude powder was dissolved in 100 ml of a 0.05M phosphate buffer (pH 6.8), and the solution was applied to a column containing 12 ml of Sephadex DEAE A-25 which had previously been equilibrated with a 0.05M phosphate buffer (pH 6.8). It was then eluted with sodium chloride solutions which were made on the basis of a 0.05M phosphate buffer (pH 6.8) to which sodium chloride was added in increasing amounts. Thus, the column was first eluted with 100 ml of a 0.1M solution, next with 100 ml of a 0.2M solution, next with 100 ml of a 0.3M solution, and finally with 100 ml of a 0.5M solution. The 0.3M sodium chloride solution was found to contain the active compounds, and this solution containing the active fractions was collected. This solution was then acidified by the addition of aqueous hydrochloric acid to adjust its pH to a value of 3.0. It was then charged onto a column containing 3 ml of active carbon, and the column was washed with 20 ml of water and eluted with 0.2 N aqueous ammonia. The eluate was concentrated by evaporation under reduced pressure, using a rotary evaporator, and the residue was lyophilized, to afford 46 mg of crude powder. The crude powder was dissolved in 1 ml of water, and analyzed by high performance liquid chromatography under the following conditions.

Separating column: YMC Pack AQ-312 (Column size, diameter 6 by 150 mm long, Yamamura Chem. Lab. Co.Ltd.)

Mobile phase: Gradient of a 0.1M phosphate buffer-4% by volume acetonitrile solution (20 minutes)

Flow rate: 1.5 ml/minute

Monitor: Detection, using a photodiode array throughout the wavelength from 230 nm to 350 nm Adenophostins A and B (produced as described in Examples 1 and 2) showed at 5.56 and 15.17 minutes, respectively, and the active substances produced by strain SANK 12177 also showed at 5.56 and 15.17 minutes (Ultraviolet Absorption 260 nm), indicating the perfect identity of the compounds produced in this Example with adenophostins A and B.

BIOLOGICAL ACTIVITY

Adenophostins A and B were characterized by their inhibitory activity on [$^3$H]-InsP$_3$ binding to rat cerebellar InsP$_3$ receptors, and the $^{45}$Ca$^{++}$ releasing activity from the endoplasmic reticulum, which was prepared from rat cerebellum.

TEST EXAMPLE 1

Inhibitory activity on [$^3$-H]-InSP$_3$ binding to InsP$_3$ receptors

The inhibitory activity of [$^3$H]-InsP$_3$ binding was assayed according to the method of Worley et al. [J. Biol. Chem. 262, 12132–12136 (1987)].

A rat cerebellar membrane fraction was homogenized in 50 mM of Tris-HCl (pH 8.0) and 1 mM of ethylenediaminetetraacetic acid, and the protein concentration in the homogenized material was adjusted to 0.6 mg/ml. 1 ml of this cerebellar homogenate was taken and 10 nM of [$^3$H]-InsP$_3$ and either adenophostin A or adenophostin B were added to it. The mixture was incubated for 5 minutes at room temperature, and then centrifuged for 5 minutes at 12,000 rpm at a temperature of 4° C. The supernatant was removed and the precipitated cerebellar membrane fraction was dissolved in 5 ml of Pico-flow (a trade name for a product of Packard Co.) to determine its radioactivity. The bound [$^3$H]-InsP$_3$ was then determined.

The activities of adenophostins A and B assayed by the procedure described above are as shown below.

IC$_{50}$ indicates the concentration required to inhibit the binding of [$^3$H]-InsP$_3$ by 50%.

The IC$_{50}$ of adenophostin A was found to be 6 nM, and the IC$_{50}$ of adenophostin B was found to be 8 nM.

TEST EXAMPLE 2

$^{45}$Ca$^{++}$ Releasing activity from the endoplasmic reticulum

The $^{45}$Ca$^{++}$ releasing activity from the endoplasmic reticulum was assayed using the method reported by Supattapone et al. [Proc. Natl, Acad. Sci. USA 85, 8747–8750 (1988)] with slight modifications.

The endoplasmic reticulum (microsome) of rat cerebellum was suspended in 10 mM of a HEPES-KOH buffer (pH 7.2) containing 100 mM of potassium chloride, 2.5 mM of magnesium chloride, 1 mM of dithiothreitol (DTT), 10 mM of creatine phosphate, creatine kinase (10 units/ml), 2 μg/ml of oligomycin, 50 μM of calcium chloride containing 1 μCi/ml of $^{45}$Ca, and 0.12 mM of ethylene glycol bis(2-aminoethyl ether)-N,N,N',N'-tetraacetic acid (EGTA), and the protein concentration in the suspension was adjusted to 0.5 mg/ml. 1 mM of adenosine triphosphate magnesium salt was added to 1 ml of this suspension, and the mixture was incubated for 11 minutes at 30° C. in order to incorporate the $^{45}$Ca++ into the endoplasmic reticulum. InsP$_3$, adenophostin A or adenophostin B was then added to release the incorporated $^{45}$Ca++ from the endoplasmic reticulum. 10 minutes after the addition of the adenosine triphosphate magnesium salt (1 minute before the addition of the adenophostins or InsP3), and then 12 minutes after the addition of the adenosine triphosphate magnesium salt (1 minute after the addition of the adenophostins or InsP3), 100 μl of the reaction solution was removed, and the sampled solution was filtered through a Milipore filter (HA, 45 μm, Product of Milipore) to collect the. endoplasmic reticulum on the filter. The filter was washed with 4 ml of a 10 mM HEPES-KOH buffer (pH 7.2) containing 100 mM of potassium chloride and 1 mM of EGTA, and the radioactivity on the filter was determined by the addition of 5 ml of Pico-flow (a trade name for a product of Packard Co.) agents.

Both adenophostin A and adenophostin B at 10 nM released 35% of the calcium ion incorporated into the endoplasmic reticulum. These activities were equal to that of InsP$_3$ at 10 μM.

From these results, it can be seen that adenophostins A and B have the ability to bind to the InsP$_3$ receptors located on the endoplasmic reticulum, to release calcium ions stored in the endoplasmic reticulum and to elevate the cytosolic calcium concentration. Accordingly, the compounds of the present invention are useful as hypertensive agents.

We claim:

1. A compound of formula (I):

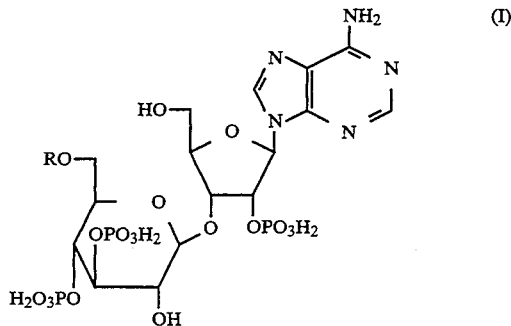

wherein R represents a hydrogen atom or an acetyl group, or a salt or ester thereof.

2. The compound of claim 1, which has the configuration shown in the following formula (Ia):

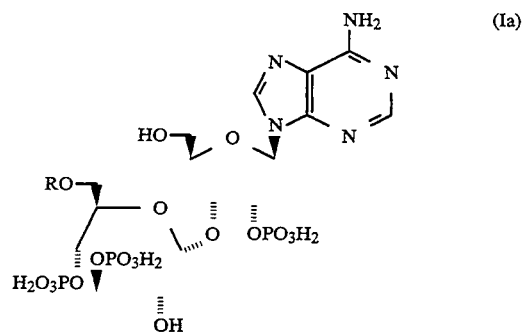

3. A pharmaceutical composition comprising a compound of formula (I) as claimed in claim 1 or a pharmaceutically acceptable salt in admixture with a pharmaceutically acceptable carrier or diluent.

4. The compound of claim 1, wherein R is a hydrogen atom or a salt thereof.

5. The compound of claim 1, wherein R is a hydrogen atom.

6. The compound of claim 1, wherein R is an acetyl group or a salt thereof.

7. The compound of claim 1, wherein R is an acetyl group.

8. The compound of claim 2, wherein R is a hydrogen atom or a salt thereof.

9. The compound of claim 2, wherein R is a hydrogen atom.

10. The compound of claim 2, wherein R is an acetyl group or a salt thereof.

11. The compound of claim 2, wherein R is an acetyl group.

* * * * *

UNITED STATES PATENT AND TRADEMARK OFFICE
CERTIFICATE OF CORRECTION

PATENT NO. : 5,436,231
DATED : July 25, 1995
INVENTOR(S) : TAKAHASHI et al

It is certified that error appears in the above-indentified patent and that said Letters Patent is hereby corrected as shown below:

Title Page, Left Column, under FOREIGN PATENT DOCUMENTS, after "1506664  4/1978" replace "Germany" with --U.K.--.

Column 9, line 4, delete "prophy-".

Column 9, lines 5-7, delete in entirety.

Column 9, line 8, delete "invention are also useful as hypertensive".

Signed and Sealed this

Eighteenth Day of November 1997

*Attest:*

BRUCE LEHMAN

*Attesting Officer*   *Commissioner of Patents and Trademarks*